United States Patent [19]
Cosserat et al.

[11] Patent Number: 5,527,975
[45] Date of Patent: Jun. 18, 1996

[54] PROCESS FOR THE PREPARATION OF BROMOCHLORO-ALKANES

[75] Inventors: Dominique Cosserat, Thann; Francois Stutz, St Amarin, both of France

[73] Assignee: Albemarle Corporation, Richmond, Va.

[21] Appl. No.: 388,044

[22] Filed: Feb. 13, 1995

[30] Foreign Application Priority Data

Apr. 21, 1994 [EP] European Pat. Off. ............ 94400865

[51] Int. Cl.$^6$ ............................ C07C 17/08; C07C 17/04
[52] U.S. Cl. .................. 570/248; 570/134; 570/246; 570/247
[58] Field of Search ........................ 570/134, 246, 570/247, 248

[56] References Cited

U.S. PATENT DOCUMENTS

| | | | |
|---|---|---|---|
| 3,330,877 | 7/1967 | Kircher et al. | 570/246 |
| 4,049,516 | 9/1977 | Gellato et al. | 204/158 |

FOREIGN PATENT DOCUMENTS

| | | | |
|---|---|---|---|
| 7214714 | 10/1973 | Netherlands | 570/216 |
| 0546600 | 2/1976 | U.S.S.R. | 570/246 |

*Primary Examiner*—Werren B. Lone
*Attorney, Agent, or Firm*—E. E. Spielman, Jr.

[57] ABSTRACT

Bromochloro-alkanes are made by reaction of a corresponding chloroalkene with hydrogen bromide by a continuous process carried at −20° to +20° C., preferably in a gas-lift reactor.

14 Claims, 1 Drawing Sheet

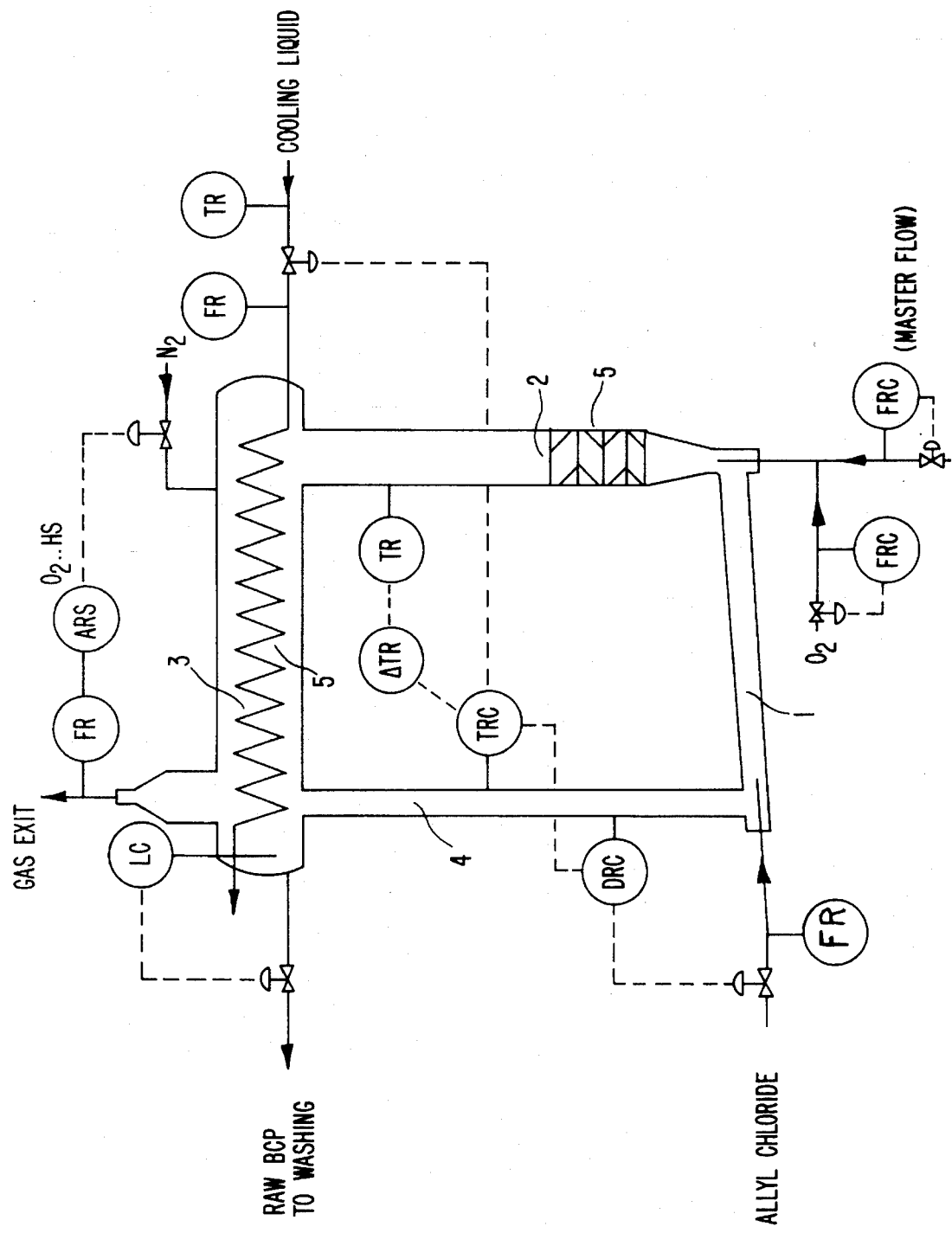

PROCESS FOR THE PREPARATION OF BROMOCHLORO-ALKANES

This invention relates to the preparation of bromochloro-alkanes, and especially 3-bromo-1-chloropropane.

3-Bromo-1-chloropropane and related bromochloro alkanes may be made by the reaction of hydrogen bromide with allyl chloride or other alkenyl chloride in the presence of a free radical-generating catalyst.

For example, U.S. Pat. No. 4,049,516 (Gellato et al) describes a continuous process for the preparation of 3-bromo-1-chloropropane. Hydrogen bromide and allyl chloride are injected into a reactor containing 10 mole % of allyl chloride and 90 mole % of 3-bromo-1-chloropropane maintained at 20°–22° C. The reaction is promoted by irradiation of the reaction mixture with a 3050 A° lamp. Reaction product is continuously withdrawn in the form of a mixture containing, in addition to the desired product, also 10% of allyl chloride and by-products. The % conversion of the allyl chloride is given as 90% and the % selectivity is given as 97%. The yield of 3-bromo-1-chloropropane is thus 87.3%, based on the allyl chloride.

East German specification 74537 (König et al) describes a batchwise or continuous process for producing 3-bromo-1-chloropropane by reaction of allyl chloride with hydrogen bromide in the presence of a peroxide catalyst. The reaction is performed initially at about 35° C. and then, after half the allyl chloride has reacted, at about 60° C.

We have now devised a continuous process for the preparation of 3-bromo-1-chloroalkanes by reaction of hydrogen bromide with a corresponding chloro-alkene in the presence of a free radical catalyst. The new process gives an excellent yield of the desired product containing reduced amounts of impurities such as dimerized products and other products of elevated molecular weight. It is moreover well adapted to automated control.

The process of the present invention for the continuous preparation of a 3-bromo-1-chloroalkane of formula

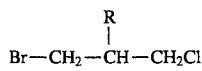

where R is hydrogen or alkyl of 1 to 4 carbon atoms, comprises (1) feeding into a first zone a chloro-alkene of formula

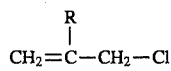

where R is hereinbefore defined, and recycled reaction products; (2) feeding the mixture obtained into a second, reaction zone and injecting hydrogen bromide, and, if required, a free radical reaction initiator into the said mixture in the said zone in such a manner that the mixture is vigorously agitated by the injected gas; (3) feeding the gas-containing mixture to a third, cooling zone in which the mixture is cooled to maintain its temperature in the range −20° to +20° C., unreacted gas is separated, and part of the reaction mixture is withdrawn for separation of the desired product; and (4) recycling the remainder of the reaction mixture to the said first zone.

The process is preferably operated as a gas lift process with the second, reaction zone constituting the up-leg of the gas lift reactor and the conduit through which the remainder of the reaction mixture is recycled to the first zone constituting the down-leg of the reactor. Use of a gas lift reactor has the advantage that relatively large amounts of starting materials can be treated in a reactor of small volume, and that the ratio of heat exchange surface to liquid volume may be kept high. Also, as explained in detail below, the process of the invention can readily be controlled when it is operated in a gas lift reactor in the way described.

Optimum yields are obtained when the reaction temperature is controlled within the range 5° to 10° C.

The free radical reaction initiator used to initiate the reaction between the hydrogen bromide and the chloroalkene is preferably an organic peroxide, e.g. benzoyl peroxide, but other free radical generating catalysts can, if desired, be used. The free radical reaction initiator is preferably introduced into the reactor in solution in the allyl chloride or other chloro-alkene.

It has been found that, once the reaction has been initiated by the use of a peroxide, typically at a concentration of about 0.1% by weight based on the weight of the chloro-alkene, or other catalyst, the reaction rate is preferably maintained by injection of oxygen into the reaction mixture along with the hydrogen bromide. Since the injected oxygen becomes partly (e.g. to the extent of about 70%) incorporated into the reaction products, the amount injected should be the minimum compatible with maintaining the desired high reaction rate. Preferably the proportion of oxygen injected is in the range from 0.3 to about 1% by volume based on the total volume of gases introduced into the reaction zone.

Hydrogen bromide is often made on a commercial scale by combustion of bromine in hydrogen. The hydrogen bromide obtained in this way usually contains a small amount of unreacted hydrogen, typically about 8 volume %. The presence of this hydrogen, which does not take part in the reaction, is not injurious, but it increases the amount of reactants and products which leave the reactor in the unreacted gas stream, and its presence may assist in promoting rapid contact between the hydrogen bromide and the chloro-alkene.

To ensure that all the chloro-alkene reacts, a small excess of hydrogen bromide is preferably used, e.g. about 5% in excess of the stoichiometric amount based on the chloro-alkene fed to the first zone.

The reaction proceeds very rapidly and with evolution of heat. It is highly desirable that the reaction shall be substantially complete in the reaction zone, and vigorous agitation of the reaction mixture in the reaction zone is therefore required. This is assisted both by the injection of the gaseous hydrogen bromide and oxygen into the reaction zone and also, preferably, by the use of static mixers to promote thorough mixing of all the reagents. When, as is preferred, the reaction zone constitutes the up-leg of a gas-lift reactor operated in bubble regime to maximize gas-liquid contact, the upward passage of the reaction mixture and gases through the reaction zone is promoted and maintained by (a) the lower density of the mixture in the up-leg (which contains dispersed gas) as compared with the reaction product in the down-leg, and (b) the somewhat higher temperature and consequent lower density of the mixture in the up-leg as compared with the product in the down-leg. As described below, this temperature differential can be used in monitoring and controlling the reaction.

In the third zone, the reaction products are cooled and unreacted gas is separated and removed. Part of the reaction mixture is then withdrawn for separation of the desired bromochloro-alkane product. The remainder is recycled to the first zone, preferably through the down-leg of the gas-lift reactor when one is used.

The desired bromochloroalkane may be isolated from the reaction products in known manner, typically by washing with caustic soda solution and water followed by fractional distillation.

BRIEF DESCRIPTION OF THE DRAWINGS

The accompanying drawing shows a gas-lift reactor constructed for operation of the new process. Use of the apparatus will be described for the reaction of allyl chloride with hydrogen bromide to produce 3-bromo-1-chloropropane, but it will be understood that other chloro alkenes can, if desired, be used in place of the allyl chloride.

In operation of the gas-lift reactor, allyl chloride is introduced into the first zone (1) where it is mixed with reaction product entering zone (1) through down-leg (4). The ratio of the rate of feed of fresh allyl chloride to zone (1) to the rate at which the recycled reaction product enters zone (1) through down-leg (4) is low, e.g. less than 1% on a weight basis. Because of the high liquid recirculation rate caused by the presence of a gas-liquid mixture in the up-leg where an exothermic reaction takes place, the gas-lift reactor acts as a continuously operated, stirred tank reactor. On an industrial scale, an injection rate of, for example, 200 to 300 kg/hr of allyl chloride may easily be achieved, with a recirculation rate of up to 40 m$^3$/hr.

The mixture of allyl chloride and recycled reaction product is then introduced into reaction zone (2) where it is mixed with the injected hydrogen bromide gas (optionally containing hydrogen) and the small amount of gaseous oxygen required to maintain the reaction rate. The weight of hydrogen bromide introduced is preferably slightly in excess of the stoichiometric amount, e.g. about 5% in excess, required to react with all the allyl chloride (or other chloro alkene) fed to the reaction zone.

The reaction mixture containing reacting allyl chloride and hydrogen bromide rises through the up-leg (2) of the gas lift apparatus into the cooling zone (3) where it contacts the cooling device (5). Unreacted gas rises to the surface of the liquid in zone (3) and is removed through the indicated gas exit. Reaction mixture is removed from zone (3) for working up at a rate such that the mean residence time of the reactor contents is 1.5 to 3.5 hours. Typically this involves removing from zone (3) in each hour 30–60% by weight of the total reactor contents. The remainder is recycled through down-leg (4) as already noted.

The cooling zone (3) is preferably of such a size that in normal operation it is about half full of liquid reaction products. This makes it possible to raise the level of the liquid, thus providing more vigorous cooling conditions, if the monitoring of the reaction temperature indicates that more cooling is required. The rate of cooling can also be controlled by controlling the rate of flow of the cooling fluid.

The reaction may be monitored in the following ways.

(1) The rate of circulation of the cooling fluid in the cooling zone is controlled by the reaction temperature (TR in the Figure) which is preferably set at 10° C. At temperatures higher than this the cooling fluid flow is increased and at lower temperatures it is reduced. Also, as noted above, the height of the liquid in the cooling zone may be controlled to increase or reduce the rate of cooling.

(2) The temperature difference between the up-leg (the reaction leg) and the down-leg (the recirculation leg) is continuously monitored. An adequate temperature difference must be maintained in order to ensure that the reactants and products circulate normally in the gas-lift reactor. If the difference in temperature is too low, this indicates that the reaction is not proceeding rapidly enough, and the reaction rate can be increased by injecting more oxygen into the reaction zone.

(3) The density of the reaction products in the down-leg is continuously monitored. Measurement of this density makes it possible to check (a) that there are no entrained gases in the reaction products in the down-leg, and (b) that the content of unreacted allyl chloride in the reaction products is sufficiently low. Since both the presence of gas and the presence of unreacted allyl chloride lower the density of the reaction products, it is thus a question of ensuring that the density of the reaction products in the down-leg is sufficiently high. Should it fall below the desired value, either the reaction rate may be increased to remove residual allyl chloride, e.g. by injection of oxygen, or the residence time of the reaction products in the cooling zone (3) can be increased to permit a longer period for the gases to leave the reaction mixture. The reaction products withdrawn from the cooling zone (3) consist mainly of the 3-bromo-1-chloroalkane with a minor amount of unreacted allyl chloride, typically equal to about 1% by weight, and small amounts of by-products. The following results obtained in laboratory scale operation compare the gas-lift process of the present invention with a reaction carried out in a stirred tank reactor. The following Table gives the reaction temperature and mean residence time of reagents in the reactor, and the yields of the products obtained. [In the Table, 2,1-BCP is 2-bromo-1-chloropropane; 1,3-BCP is 1-bromo-3-chloropropane; DBP is dibromopropane; DBCP is dibromochloropropane.]

TABLE

| Reactor | Temperature (°C.) | Mean residence time (h) | Yield on allyl chloride | Composition of the product obtained (Weight %) | | | | | | |
|---|---|---|---|---|---|---|---|---|---|---|
| | | | | Light Compounds | 2,1-BCP | 1,3-BCP | DBP | DBCP | Dimer | Heavy compounds |
| Stirred tank reactor | 25 | 4 | 93.0 | 0.25 | 4.65 | 93.0 | 0.15 | 0.45 | 0.30 | 0.25 |
| Gas-lift recycle factor | 25 | 2 | 91.5 | 0.15 | 4.5 | 93.0 | 0.05 | 0.15 | 0.35 | 0.20 |
| | 13 | 2 | 93 | 0.50 | 3.9 | 94.1 | 0.05 | 0.10 | 0.25 | 0.15 |
| | 9 | 2 | 94 | 0.10 | 3.7 | 94.7 | 0.05 | 0.10 | 0.25 | 0.10 |
| | 1 | 3.5 | 94 | 0.45 | 3.4 | 94.4 | 0.05 | 0.10 | 0.30 | 0.30 |

These results show that the process of the present invention, operated at temperatures in the range of about 0° to 15° C., gives a 3-bromo-1-chloropropane product which is significantly purer than the product obtained either with a stirred tank reactor or in a gas-lift reactor at 25° C. It will be noted also that the content of dimer and heavy compounds is significantly less with the process carried out in accordance with the present invention.

What is claimed is:

1. Continuous process for the preparation of a 3-bromo-1-chloro-alkane of formula:

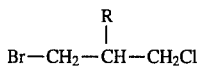

where R is hydrogen or alkyl of 1 to 4 carbon atoms which comprises (1) feeding into a first zone a chloro-alkene of formula:

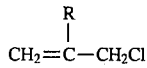

where R is as hereinbefore defined, and recycled reaction products; (2) feeding the mixture obtained in to a second reaction zone and injecting gaseous hydrogen bromide in such a manner that the mixture is vigorously agitated by the injected gas; (3) feeding the gas-containing mixture to a third, cooling zone in which the mixture is cooled to maintain its temperature in the range −20° to +20° C., unreacted gas is separated and part of the reaction mixture is withdrawn for separation of the desired product; and (4) recycling the remainder of the reaction mixture to the first zone.

2. A process according to claim 1 in which R is hydrogen.

3. A process according to claim 1 in which the reaction temperature is 5° to 10° C.

4. A process according to claim 1 in which the amount of hydrogen bromide injected is about 5% in excess of the stoichiometric amount, based on the chloro-alkene feed to the first zone.

5. A process according to claim 1 in which the reaction is performed at ambient pressure.

6. A process according to claim 1 in which oxygen is fed to the reaction zone, the volume of oxygen being about 0.3 to 1% based on the total volume of gases introduced.

7. A process according to claim 1 in which the process is operated in a gas-lift reactor, the reaction zone constituting the up-leg of the reactor and recycling conduit from the cooling zone to the first zone constituting the down-leg of the reactor.

8. A process according to claim 1 wherein, in step (2), a free radical reaction initiator is injected into the mixture in the zone.

9. A process according to claim 8 in which R is hydrogen.

10. A process according to claim 8 in which the reaction temperature is 5° to 10° C.

11. A process according to claim 8 in which the amount of hydrogen bromide injected is about 5% in excess of the stoichiometric amount, based on the chloro-alkene fed to the first zone.

12. A process according to claim 8 in which the reaction is performed at ambient pressure.

13. A process according to claim 8 in which oxygen is fed to the reaction zone, the volume of oxygen being about 0.3 to 1% based on the total volume of gases introduced.

14. A process according to claim 8 in which the process is operated in a gas-lift reactor, the reaction zone constituting the up-leg of the reactor and recycling conduit from the cooling zone to the first zone constituting the down-leg of the reactor.

* * * * *